(12) United States Patent
Meguro et al.

(10) Patent No.: US 11,953,510 B2
(45) Date of Patent: Apr. 9, 2024

(54) MANAGEMENT SYSTEM AND MANAGEMENT METHOD

(71) Applicant: FUJIFILM CORPORATION, Tokyo (JP)

(72) Inventors: Takeya Meguro, Kanagawa (JP); Kazuhiro Hirota, Kanagawa (JP); Yoshihiro Seto, Kanagawa (JP); Kaku Irisawa, Kanagawa (JP); Hirotaka Watano, Kanagawa (JP); Taiji Iwasaki, Kanagawa (JP); Tatsuyuki Denawa, Kanagawa (JP); Haruyasu Nakatsugawa, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 445 days.

(21) Appl. No.: 17/372,551

(22) Filed: Jul. 12, 2021

(65) Prior Publication Data

US 2022/0018864 A1 Jan. 20, 2022

(30) Foreign Application Priority Data

Jul. 15, 2020 (JP) .................... 2020-121721

(51) Int. Cl.
*G06T 7/00* (2017.01)
*G01N 33/49* (2006.01)
(Continued)

(52) U.S. Cl.
CPC ....... *G01N 35/00732* (2013.01); *G01N 33/49* (2013.01); *G06T 7/0012* (2013.01); *G01N 2035/00831* (2013.01)

(58) Field of Classification Search
USPC ....... D24/107–234; 382/128–224; 706/1–62, 706/900–903
See application file for complete search history.

(56) References Cited

U.S. PATENT DOCUMENTS

2015/0209114 A1* 7/2015 Burkholz ............... G06V 20/20
600/584
2016/0378954 A1* 12/2016 Kitagawa ............... G16H 10/40
435/287.2
(Continued)

FOREIGN PATENT DOCUMENTS

JP 2006-011918 A 1/2006
JP 2008-249359 A 10/2008
(Continued)

OTHER PUBLICATIONS

Sasaki Toshiyuki; Analyzer and Analytical Method; Sep. 25, 2008 (Year: 2008).*
(Continued)

*Primary Examiner* — Marcellus J Augustin
(74) *Attorney, Agent, or Firm* — SOLARIS Intellectual Property Group, PLLC

(57) ABSTRACT

A management system including at least one processor, wherein the processor is configured to acquire an image obtained by imaging a sample container containing a sample, recognize relevant information related to reliability of a test result related to the sample based on the image, and derive reliability information indicating the reliability of the test result related to the sample based on the recognized relevant information.

16 Claims, 17 Drawing Sheets

(51) Int. Cl.
  *G01N 35/00* (2006.01)
  *G01N 35/10* (2006.01)

(56) References Cited

U.S. PATENT DOCUMENTS

2017/0185815 A1\* 6/2017 Itoh ..................... G06K 7/1413
2018/0128806 A1   5/2018 Yamashita et al.

FOREIGN PATENT DOCUMENTS

| JP | 2014-212724 A | 11/2014 |
| JP | 2017-120206 A | 7/2017 |
| WO | 2010/140680 A1 | 12/2010 |
| WO | 2017/006961 A1 | 1/2017 |

OTHER PUBLICATIONS

Bolander Jarie G; RFID Tracking of Patient Specimen Samples; May 20, 2010 (Year: 2010).\*
Ariyoshi Shunsuke; Sample Processing Apparatus And Non-transitory Storage Medium; May 2, 2012 (Year: 2012).\*
Menhardt Wido; History Logging for Samples of Biological Material; Jan. 4, 2018 (Year: 2018).\*
Ito Hiroaki; Specimen Management System; Jul. 4, 2013 (Year: 2013).\*
English language translation of the following: Office action dated Apr. 18, 2023 from the JPO in a Japanese patent application No. 2020-121721 corresponding to the instant patent application. This office action translation is submitted now in order to supplement the understanding of the cited references which are being disclosed in the instant Information Disclosure Statement.

\* cited by examiner

FIG. 6

TEST ORDER (COMPANY P)

| SUBJECT ID | NAME | GENDER | AGE |
|---|---|---|---|
| P101 | ICHIRO FUJI | MALE | 37 |
| P102 | TARO SANYO | MALE | 25 |
| ⋮ | ⋮ | ⋮ | ⋮ |

TEST ORDER (COMPANY Q)

| SUBJECT ID | NAME | GENDER | AGE |
|---|---|---|---|
| Q101 | ICHIRO FUJI | MALE | 50 |
| Q102 | JIRO SANYO | MALE | 21 |
| Q103 | HANAKO FUJI | FEMALE | 29 |
| ⋮ | ⋮ | ⋮ | ⋮ |

FIG. 7

| | | |
|---|---|---|
| NAME ICHIRO FUJI (MALE)/FEMALE 37 YEARS OLD | | ○ 70 ○ 60 ● 50 |
| 4 MONTH 25 DAY 2019 YEAR 18 HOUR | | |
| NAME TARO SANYO (MALE)/FEMALE 25 YEARS OLD | | ○ 70 ○ 60 ● 50 |
| 4 MONTH 22 DAY 2019 YEAR 10 HOUR | | |
| NAME HANAKO FUJI MALE/(FEMALE) 29 YEARS OLD | | ○ 70 ○ 60 ○ 50 |
| 4 MONTH 26 DAY 2019 YEAR 6 HOUR | | |
| NAME ICHIRO FUJI (MALE)/FEMALE 50 YEARS OLD | | ○ 70 ○ 60 ○ 50 |
| 4 MONTH 26 DAY 2019 YEAR 7 HOUR | | |
| NAME JIRO SANYO (MALE)/FEMALE 21 YEARS OLD | | ○ 70 ○ 60 ○ 50 |
| 4 MONTH 19 DAY 2019 YEAR 7 HOUR | | |

FIG. 8

IMAGE AND TEST RESULT

| TEST ID | IMAGE | MEASURED VALUE |
|---|---|---|
| 0001 | NAME ICHIRO FUJI (MALE)/FEMALE 37 YEARS OLD / 4 MONTH 25 DAY 2019 YEAR 18 HOUR | 5 |
| 0002 | NAME TARO SANYO (MALE)/FEMALE 25 YEARS OLD / 4 MONTH 22 DAY 2019 YEAR 10 HOUR | 8 |
| 0003 | NAME HANAKO FUJI MALE/(FEMALE) 29 YEARS OLD / 4 MONTH 26 DAY 2019 YEAR 6 HOUR | 0 |
| 0004 | NAME ICHIRO FUJI (MALE)/FEMALE 50 YEARS OLD / 4 MONTH 26 DAY 2019 YEAR 7 HOUR | 101 |
| 0005 | NAME JIRO SANYO (MALE)/FEMALE 21 YEARS OLD / 4 MONTH 19 DAY 2019 YEAR 7 HOUR | 6 |
| ⋮ | ⋮ | ⋮ |

| TEST ID | RECOGNITION RESULT AND DERIVATION RESULT | | | | COLLECTION DATE | MAXIMUM-REACHED TEMPERATURE | DEGREE OF RELIABILITY |
|---|---|---|---|---|---|---|---|
| | IMAGE | NAME | GENDER | AGE | | | |
| 0001 | NAME ICHIRO FUJI (MALE) 37 YEARS OLD / 4 MONTH 25 DAY 2019 YEAR 18 HOUR / ○70 ○60 ●50 | ICHIRO FUJI | MALE | 37 | 4/25/2019 18:00 | 50 | 80 |
| 0002 | NAME TARO SANYO (MALE) 25 YEARS OLD / 4 MONTH 22 DAY 2019 YEAR 10 HOUR / ○70 ○60 ●50 | TARO SANYO | MALE | 25 | 4/22/2019 10:00 | 50 | 60 |
| 0003 | NAME HANAKO FUJI (FEMALE) 29 YEARS OLD / 4 MONTH 26 DAY 2019 YEAR 6 HOUR / ○70 ○60 ○50 | HANAKO FUJI | FEMALE | 29 | 4/26/2019 6:00 | – | 100 |
| 0004 | NAME ICHIRO FUJI (MALE) 50 YEARS OLD / 4 MONTH 26 DAY 2019 YEAR 7 HOUR / ○70 ○60 ○50 | ICHIRO FUJI | MALE | 50 | 4/26/2019 7:00 | – | 100 |
| 0005 | NAME JIRO SANYO (MALE) 21 YEARS OLD / 4 MONTH 19 DAY 2019 YEAR 7 HOUR / ○70 ○60 ○50 | JIRO SANYO | MALE | 21 | 4/19/2019 7:00 | – | 50 |
| ... | ... | ... | ... | ... | ... | ... | ... |

FIG. 10

FECAL OCCULT BLOOD TEST  T1

| MAXIMUM-REACHED TEMPERATURE \ NUMBER OF ELAPSED DAYS | 0 TO 6 | 7 TO 9 | 10 TO |
|---|---|---|---|
| - | 100 | 80 | 50 |
| 50 | 80 | 60 | 30 |
| 60 | 70 | 50 | 20 |
| 70 | 60 | 40 | 10 |

BLOOD TEST  T2

| MAXIMUM-REACHED TEMPERATURE \ NUMBER OF ELAPSED DAYS | 0 TO 3 | 4 TO 5 | 6 TO |
|---|---|---|---|
| - | 100 | 80 | 50 |
| 50 | 95 | 75 | 45 |
| 60 | 90 | 70 | 40 |
| 70 | 85 | 65 | 35 |

FIG. 11

RECOGNITION RESULT, TEST RESULT AND DERIVATION RESULT

| TEST ID | IMAGE | NAME | GENDER | AGE | MEASURED VALUE | DEGREE OF RELIABILITY |
|---------|-------|------|--------|-----|----------------|----------------------|
| 0001 | NAME ICHIRO FUJI  MALE/FEMALE 37 YEARS OLD  4 MONTH 25 DAY 2019 YEAR 18 HOUR   55  ○70 ○60 ●50 | ICHIRO FUJI | MALE | 37 | 5 | 80 |
| 0002 | NAME TARO SANYO  MALE/FEMALE 25 YEARS OLD  4 MONTH 22 DAY 2019 YEAR 10 HOUR   ○70 ○60 ●50 | TARO SANYO | MALE | 25 | 8 | 60 |
| 0003 | NAME HANAKO FUJI  MALE/FEMALE 29 YEARS OLD  4 MONTH 26 DAY 2019 YEAR 6 HOUR   ○70 ○60 ○50 | HANAKO FUJI | FEMALE | 29 | 0 | 100 |
| 0004 | NAME ICHIRO FUJI  MALE/FEMALE 50 YEARS OLD  4 MONTH 26 DAY 2019 YEAR 7 HOUR   ○70 ○60 ○50 | ICHIRO FUJI | MALE | 50 | 101 | 100 |
| 0005 | NAME JIRO SANYO  MALE/FEMALE 21 YEARS OLD  4 MONTH 19 DAY 2019 YEAR 7 HOUR   ○70 ○60 ○50 | JIRO SANYO | MALE | 21 | 6 | 50 |
| ... | ... | ... | ... | ... | ... | ... |

108 = {DEGREE OF RELIABILITY column}

TEST ORDER (COMPANY P)

| SUBJECT ID | NAME | GENDER | AGE |
|------------|------|--------|-----|
| P101 | ICHIRO FUJI | MALE | 37 |
| P102 | TARO SANYO | MALE | 25 |
| ... | ... | ... | ... |

TEST ORDER (COMPANY Q)

| SUBJECT ID | NAME | GENDER | AGE |
|------------|------|--------|-----|
| Q101 | ICHIRO FUJI | MALE | 50 |
| Q102 | JIRO SANYO | MALE | 21 |
| Q103 | HANAKO FUJI | FEMALE | 29 |
| ... | ... | ... | ... |

FIG. 12

TEST RESULT REPORT

Company P

| SUBJECT ID | NAME | GENDER | AGE | TEST ID | IMAGE | MEASURED VALUE | DEGREE OF RELIABILITY | COMMENT |
|---|---|---|---|---|---|---|---|---|
| P101 | ICHIRO FUJI | MALE | 37 | 0001 | NAME ICHIRO FUJI (MALE) 37 YEARS OLD  4 MONTH 25 DAY 2019 YEAR 18 HOUR  55 | 5 | 80 | THIS TEST RESULT IS LIKELY TO BE INACCURATE. PLEASE CONSIDER RETEST. |
| P102 | TARO SANYO | MALE | 25 | 0002 | NAME TARO SANYO (MALE) 25 YEARS OLD  4 MONTH 22 DAY 2019 YEAR 10 HOUR | 8 | 60 | THIS TEST RESULT IS LIKELY TO BE INACCURATE. PLEASE CONSIDER RETEST. |
| ... | ... | ... | ... | ... | ... | ... | ... | ... |

Company Q

| SUBJECT ID | NAME | GENDER | AGE | TEST ID | IMAGE | MEASURED VALUE | DEGREE OF RELIABILITY | COMMENT |
|---|---|---|---|---|---|---|---|---|
| Q101 | ICHIRO FUJI | MALE | 50 | 0004 | NAME ICHIRO FUJI (MALE) 50 YEARS OLD  4 MONTH 26 DAY 2019 YEAR 7 HOUR | 101 | 100 | THIS TEST RESULT IS ACCURATE. |
| Q102 | JIRO SANYO | MALE | 21 | 0005 | NAME JIRO SANYO (MALE) 21 YEARS OLD  4 MONTH 19 DAY 2019 YEAR 7 HOUR | 6 | 50 | THIS TEST RESULT IS HIGHLY LIKELY TO BE INACCURATE. PLEASE PERFORM RETEST. |
| Q103 | HANAKO FUJI | FEMALE | 29 | 0003 | NAME HANAKO FUJI (FEMALE) 29 YEARS OLD  4 MONTH 26 DAY 2019 YEAR 6 HOUR | 0 | 100 | THIS TEST RESULT IS ACCURATE. |
| ... | ... | ... | ... | ... | ... | ... | ... | ... |

FIG. 17

| TEST ID | RECOGNITION RESULT AND DERIVATION RESULT 38 | NAME | GENDER | AGE | AFFILIATION | COLLECTION DATE | MAXIMUM-REACHED TEMPERATURE | DEGREE OF RELIABILITY |
|---|---|---|---|---|---|---|---|---|
| 0001 | NAME ICHIRO FUJI MALE/FEMALE 37 YEARS OLD  4 MONTH 25 DAY 2019 YEAR 18 HOUR  P ○70 ○60 ●55 | ICHIRO FUJI | MALE | 37 | P | 4/25/2019 18:00 | 50 | 80 |
| 0002 | NAME TARO SANYO MALE/FEMALE 25 YEARS OLD  4 MONTH 22 DAY 2019 YEAR 10 HOUR | TARO SANYO | MALE | 25 | P | 4/22/2019 10:00 | 50 | 60 |
| 0003 | NAME HANAKO FUJI MALE/FEMALE 29 YEARS OLD  4 MONTH 26 DAY 2019 YEAR 6 HOUR  Q | HANAKO FUJI | FEMALE | 29 | Q | 4/26/2019 6:00 | - | 100 |
| 0004 | NAME ICHIRO FUJI MALE/FEMALE 50 YEARS OLD  4 MONTH 26 DAY 2019 YEAR 7 HOUR | ICHIRO FUJI | MALE | 50 | Q | 4/26/2019 7:00 | - | 100 |
| 0005 | NAME JIRO SANYO MALE/FEMALE 21 YEARS OLD  4 MONTH 19 DAY 2019 YEAR 7 HOUR  ○70 ○60 ○50 | JIRO SANYO | MALE | 21 | Q | 4/19/2019 7:00 | - | 50 |
| ... | ... | ... | ... | ... | ... | ... | ... | ... |

FIG. 18

| NAME | MALE FEMALE | YEARS OLD |
| MONTH | DAY | YEAR | HOUR |

NAME ICHIRO FUJI (MALE)/FEMALE 37 YEARS OLD  ○ 70  ○ 60  ● 50
4 MONTH 25 DAY 2019 YEAR 18 HOUR

NAME TARO SANYO (MALE)/FEMALE 25 YEARS OLD
4 MONTH 22 DAY 2019 YEAR 10 HOUR

| NAME | MALE FEMALE | YEARS OLD |
| MONTH | DAY | YEAR | HOUR |

NAME HANAKO FUJI MALE/(FEMALE) 29 YEARS OLD
4 MONTH 26 DAY 2019 YEAR 6 HOUR

NAME ICHIRO FUJI (MALE)/FEMALE 50 YEARS OLD
4 MONTH 26 DAY 2019 YEAR 7 HOUR

NAME JIRO SANYO (MALE)/FEMALE 21 YEARS OLD  ○ 70  ○ 60  ● 50
4 MONTH 26 DAY 2019 YEAR 7 HOUR

| NAME | MALE FEMALE | YEARS OLD |
| MONTH | DAY | YEAR | HOUR |

MANAGEMENT SYSTEM AND MANAGEMENT METHOD

CROSS-REFERENCE TO RELATED APPLICATIONS

The present application claims priority under 35 U.S.C. § 119 to Japanese Patent Application No. 2020-121721, filed on Jul. 15, 2020. The above application is hereby expressly incorporated by reference, in its entirety, into the present application.

BACKGROUND

Technical Field

The present disclosure relates to a management system and a management method.

Related Art

In the related art, various tests such as a fecal occult blood test and a blood test have been performed. In some of these tests, for example, an institution that performs a test such as a testing institution and an institution that uses the test results such as a hospital may be different.

For example, in the case of a fecal occult blood test, a subject collects a sample such as feces and submits it to the hospital. The hospital provides the testing institution with a test order including information such as name, gender, and age to specify each subject, as well as samples submitted by plural subjects. The testing institution performs tests on each of plural samples provided by the hospital, and notifies the hospital and/or the subject by associating the subject with the test result, based on the test order received from the hospital.

That is, the testing institution is performing the work of associating the test result related to the sample in a sample container containing the sample with the test order. In the related art, this work has been performed by a method such as manually attaching a barcode or the like issued based on a test order to a corresponding sample container of a subject and reading the barcode at the time of testing the sample.

For example, WO2010/140680A discloses a technique in which sample information such as a patient's name and a sample collection date and time is visually displayed on a test cartridge container containing a sample, the displayed contents are imaged with a digital camera to obtain image data, and the sample information is analyzed from the image data. Further, for example, JP2008-249359A discloses that the name and identification information of an examinee and the matters specially described about the sample are set as a barcode and attached to the corresponding sample container, and the barcode is read in a case where the examinee and the test data are associated with each other.

In addition, there are plural types of blood collection tubes used in blood tests, such as those for biochemical tests (liver function, renal function, and the like), blood tests (erythrocytes, white blood cells, and the like), and blood glucose tests, each of which has a different encapsulated reagent. JP2006-011918A discloses a technique for preventing the use of the wrong type of blood collection tube and the blood collection tube whose medicine has expired by attaching a label containing information on the type of blood collection tube, the expiration date of the blood collection tube, and the like to the blood collection tube in advance and reading the label before blood collection.

SUMMARY

Incidentally, for samples such as feces and blood, in a case where the elapsed time from the sample collection date to the test implementation date and the environment such as the temperature at which the sample is placed are inappropriately managed, the sample will change qualitatively, resulting in an unsuitable sample for which an appropriate test result cannot be obtained. That is, in a case where the sample is not appropriately managed between the time when the sample is collected and the time when the test is performed, the reliability of the test result related to the sample is lowered. Therefore, there is a demand for a technique capable of deriving information indicating appropriateness as a sample, that is, reliability of test results, in a case where a test is performed at a testing institution.

The present disclosure has been made in view of the above circumstances, and an object of the present disclosure is to provide a management system and a management method capable of deriving information indicating the reliability of test results.

A management system according to an aspect of the present disclosure comprises at least one processor. The processor is configured to acquire an image obtained by imaging a sample container containing a sample, recognizes relevant information related to reliability of a test result related to the sample based on the image, and derive reliability information indicating the reliability of the test result related to the sample based on the recognized relevant information.

In the management system according to the aspect of the present disclosure, collection date information indicating a collection date on which the sample contained in the sample container is collected may be given to an outer surface of the sample container, and the processor may be configured to recognize the collection date information included in the image as the relevant information, and derive the reliability information based on the recognized collection date information.

In the management system according to the aspect of the present disclosure, a temperature detection material which irreversibly indicates a maximum-reached temperature in an environment in which the sample container is placed may be given to the sample container, and the processor may be configured to recognize information on the maximum-reached temperature included in the image as the relevant information, and derive the reliability information based on the recognized information on the maximum-reached temperature.

In the management system according to the aspect of the present disclosure, in a case where plural the sample containers are divided into groups, the temperature detection material may be given to at least one sample container included in the group, and the processor may be configured to derive the reliability information by using the recognized information on the maximum-reached temperature for the sample container to which the temperature detection material is given as information on a maximum-reached temperature for the other sample container included in the group including the sample container.

In the management system according to the aspect of the present disclosure, the sample container may include a transparent portion which is at least a part of the sample container and is formed to be transparent or translucent so that at least one of an amount or a color of the sample contained in the sample container is checked, and the processor may be configured to recognize at least one information of the amount or the color of the sample checked in the transparent portion included in the image as the relevant information, and derive the reliability information based on the recognized at least one information of the amount or the color of the sample.

The management system according to the aspect of the present disclosure may further comprise a table in which derivation criteria for deriving the reliability information based on the relevant information are recorded for each type of the sample, and the processor may be configured to derive reliability information of a test result related to a corresponding sample based on the derivation criteria recorded in the table.

In the management system according to the aspect of the present disclosure, the processor may be configured to perform control such that the test result and the reliability information are displayed on a display in association with each other.

In the management system according to the aspect of the present disclosure, the processor may be configured to perform control such that the test result and a comment added based on the reliability information related to the test result are displayed on a display in association with each other.

In the management system according to the aspect of the present disclosure, the processor may be configured to determine whether or not to perform a test related to the sample contained in the sample container based on the reliability information.

In the management system according to the aspect of the present disclosure, subject information of a subject from whom the sample contained in the sample container is collected may be given to an outer surface of the sample container, and the processor may be configured to acquire an image obtained by imaging an area including the subject information given to the sample container, recognize the subject information given to the sample container based on the image, and associate a test result related to the sample contained in each of the sample containers with a test order including the subject information, based on the recognized subject information and the test order.

In the management system according to the aspect of the present disclosure, the processor may be configured to acquire an image obtained by imaging an outer surface of a boundary container in which group boundary information indicating a boundary between plural groups is given to the outer surface in a case where plural the sample containers are divided into groups and samples are continuously tested for the plurality of groups, recognize the group boundary information given to the boundary container based on the image, and associate the test result related to the sample contained in each of the sample containers with a test order in which the group is divided corresponding to the group boundary information, based on the recognized group boundary information and the test order.

In the management system according to the aspect of the present disclosure, the boundary container may be a sample container containing a sample to be tested at at least one of first or last in the group.

In the management system according to the aspect of the present disclosure, the boundary container may be a dummy container which does not contain a sample.

In the management system according to the aspect of the present disclosure, the group boundary information may include group discrimination information for discriminating a group to which the sample container belongs, and the processor may be configured to further recognize the group discrimination information based on the image, and associate the test result related to the sample contained in each of the sample containers with the test order further including the group discrimination information, based on the recognized group discrimination information and the test order.

In the management system according to the aspect of the present disclosure, the group boundary information may be represented by at least one of a character or a symbol.

In the management system according to the aspect of the present disclosure, a fact that subject information is not entered on an outer surface of the dummy container may be used as the group boundary information.

In the management system according to the aspect of the present disclosure, the processor may be configured to perform control such that the test result and the test order are displayed on a display in association with each other.

A management method according to another aspect of the present disclosure comprises acquiring an image obtained by imaging a sample container containing a sample, recognizing relevant information related to reliability of a test result related to the sample based on the image, and deriving reliability information indicating the reliability of the test result related to the sample based on the recognized relevant information.

According to the aspects of the present disclosure, it is possible to provide a management system and a management method capable of deriving information indicating reliability of a test result.

BRIEF DESCRIPTION OF THE DRAWINGS

FIG. 6 is a diagram showing an example of a test order.

FIG. 7 is a diagram showing an example of a state in which a sample container is housed in a rack.

FIG. 8 is a diagram showing an example of a test result and an image obtained by imaging a sample container.

FIG. 9 is a diagram showing an example of a recognition result of an image and a derivation result obtained by imaging a sample container.

FIG. 10 is a diagram showing an example of a table used for deriving reliability information.

FIG. 11 is a diagram showing a process of associating a test result with a test order.

FIG. 12 is a diagram showing an example of a screen in which a test result and a test order are displayed in association with each other.

FIG. 17 is a diagram showing an example of a recognition result of an image and a derivation result obtained by imaging a sample container.

FIG. 18 is a diagram showing an example of a dummy container to which group boundary information is given.

FIG. 19 is a diagram showing an example of a dummy container to which group boundary information is given.

FIG. 20 is a diagram showing an example of a dummy container to which group boundary information is given.

FIG. 21 is a diagram showing an example of a dummy container to which group boundary information is given.

DESCRIPTION OF EMBODIMENTS

Hereinafter, each embodiment of the present disclosure will be described in detail with reference to the drawings.

First Embodiment

Figure 1:
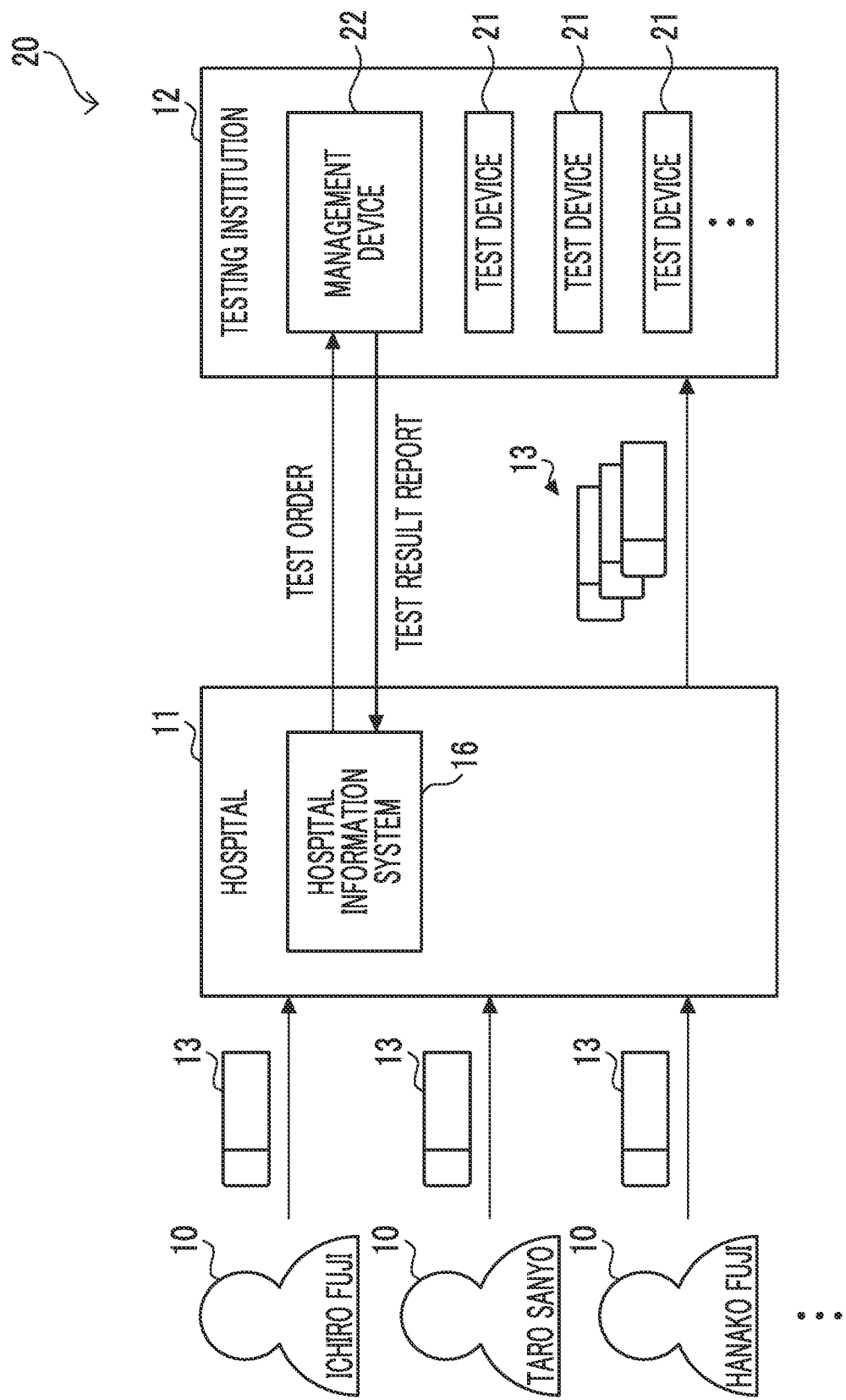
FIG. 1 is a diagram showing an example of a configuration of a management system according to each embodiment.

First, the configuration of a management system 20 of the present disclosure will be described with reference to FIG. 1. As shown in FIG. 1, in various medical-related tests such as a fecal occult blood test or a blood test (hereinafter, simply referred to as a "test"), a hospital 11 visited by a subject 10 for a health diagnosis, other tests, or diagnosis, and a testing institution 12 which is a separate organization from the hospital 11 are involved.

The subject 10 collects a sample to be used for the test, contains the collected sample in a dedicated container (hereinafter, referred to as a "sample container") 13, and submits it to the hospital 11. The sample is the body tissue or secretions of the subject 10. For example, in the fecal occult blood test, the sample is the feces of the subject 10. In the blood test, the sample is the blood of the subject 10. Hereinafter, for the sake of description, it is assumed that the test to be performed is specifically a fecal occult blood test.

On the other hand, the hospital 11 usually requests a test to the testing institution 12, which is a specialized institution for a test. For example, the hospital 11 issues a test request (hereinafter, referred to as a "test order"; details will be described later) to the testing institution 12 by using a hospital information system (HIS) 16 or the like. Further, the hospital 11 sends the sample container 13 containing the sample to the testing institution 12.

Figure 2:
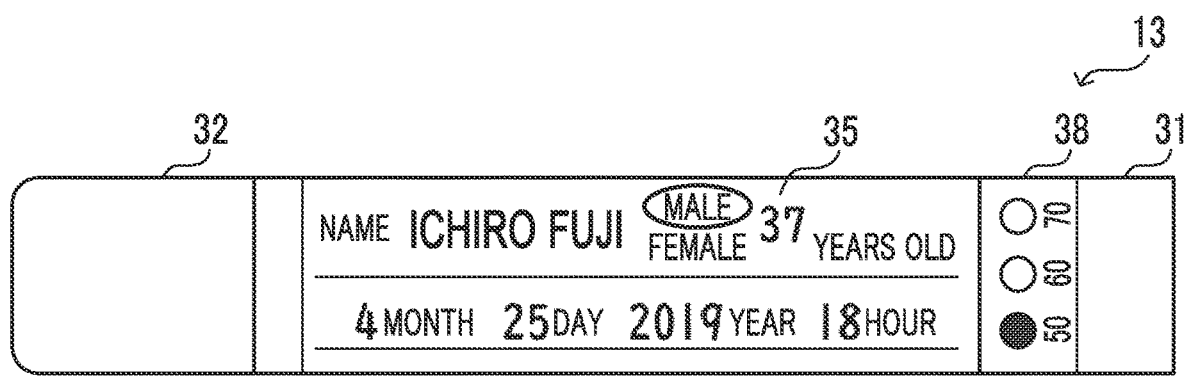
FIG. 2 is a diagram showing an example of a sample container for a fecal occult blood test.

FIG. 2 is a diagram showing a stool collection container as an example of the sample container 13. The sample container 13 is a container made into a kit so that the subject 10 can collect stool by himself/herself and store it stably for a certain period of time. As shown in FIG. 2, the sample container 13 comprises a container body 31 for containing feces as a sample, and a cap 32 attachably and detachably provided on the container body 31. The container body 31 is, for example, transparent or translucent, and contains a diluent and/or a storage solution of feces as a sample therein. An insertion part (not shown) to be inserted into the container body 31 is attached to the cap 32. Therefore, the subject 10 removes the cap 32 from the container body 31, collects feces by tracing the surface of the feces as a sample with the distal end of the insertion part, inserts the insertion part into the container body 31, and closes the cap 32 to thereby collect the feces as a sample.

In the sample container 13, a label 35 is attached to the outer surface of the container body 31, and the subject 10 can enter various information including his/her own name information on the label 35. That is, information of the subject from whom the sample contained in the sample container 13 is collected (hereinafter, referred to as "subject information") is given to the outer surface of the sample container 13. In the example of FIG. 2, the label 35 is given information on the name ("Ichiro Fuji" in FIG. 2), gender ("male" in FIG. 2), and age ("37 years old" in FIG. 2) as an example of the subject information.

Incidentally, for samples such as feces and blood contained in the sample container 13, in a case where the elapsed time from the sample collection date to the test implementation date and the environment such as the temperature at which the sample is placed are inappropriately managed, the sample will change qualitatively, resulting in an unsuitable sample for which an appropriate test result cannot be obtained. That is, in a case where the sample is not appropriately managed between the time when the sample is collected and the time when the test is performed, the reliability of the test result related to the sample is lowered.

Therefore, relevant information related to the reliability of the test result related to the sample contained in the sample container 13 is given to the outer surface of the sample container 13 according to the present embodiment. As described above, the relevant information is information regarding factors which may reduce the reliability of the test result related to the sample, such as the elapsed time from the sample collection date to the test implementation date and the environment such as the temperature at which the sample is placed.

In the example of FIG. 2, as an example of relevant information, collection date information ("month: 4 day: 25 year: 2019 hour: 18" in FIG. 2) indicating a collection date on which the sample contained in the sample container 13 is collected is given to the label 35 attached to the outer surface of the sample container 13.

Further, in the example of FIG. 2, a temperature detection material 38 which irreversibly indicates a maximum-reached temperature in an environment in which the sample container is placed is given to the sample container 13. The temperature detection material 38 is, as an example of relevant information, a member which clearly indicates information on the maximum-reached temperature in the environment in which the sample container 13 is placed, and is realized, for example, by Thermolabel (registered trademark) or the like using a material which discolors in a case where the material reaches a specific temperature and which does not return color even in a case cooled. In the temperature detection material 38 shown in FIG. 2, since the temperature indicating portion corresponding to 50 degrees is discolored, and the temperature indicating portion corresponding to 60 degrees and 70 degrees is not discolored, it is clearly indicated that the maximum-reached temperature in the environment in which the sample container 13 is placed is 50 degrees or higher and lower than 60 degrees.

Since the fecal occult blood test is usually performed using feces for two days, two types of labels 35 in different colors may be used to distinguish the sample containers 13 for two days related to the same person. For example, in FIG. 2, the characters indicating the name entry field ("name"), the characters indicating the gender selection field ("male" and "female"), the characters indicating the age entry field ("years old"), the characters indicating the collection date entry field ("month", "day", "year", and "hour"), and/or other ruled lines may be different in color. Hereinafter, for the sake of simplification of the description, only one sample container 13 related to the same subject 10 will be described.

The testing institution 12 comprises at least one test device 21, and a management device 22. The management system 20 according to an aspect of the present disclosure includes the management device 22 and some or all of the test devices 21. The testing institution 12 may comprise plural types of test devices 21 depending on the type of test to be performed. For example, in a case where the testing institution 12 supports a fecal occult blood test and a blood test, it may comprise two types of test devices 21, a fecal occult blood test device and a blood test device.

Figure 3:
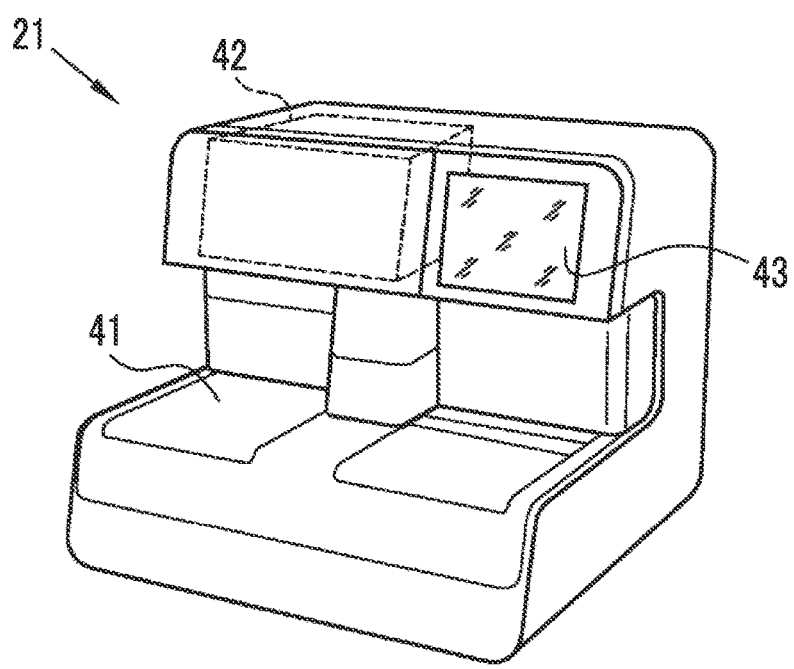
FIG. 3 is a perspective view showing an example of a fecal occult blood test device (test device).

FIG. 3 is a perspective view showing a fecal occult blood test device as an example of the test device 21. The test device 21 comprises a sample container placing portion 41, a test unit 42 which is a substantive mechanism for performing a test, and a touch panel 43 which functions as an operation unit and a display unit of the test device 21. The test device 21 includes, for example, a central processing unit (CPU), a read only memory (ROM), a random access memory (RAM), and the like.

The sample container placing portion 41 is a portion on which one or plural sample containers 13 are placed in a case of performing a test. In the present embodiment, as shown in FIG. 7, plural sample containers 13 are set in a rack 46 that holds a portion related to subject information and relevant information in a state of not being hidden in the rack 46, and the plurality of sample containers 13 are placed on the sample container placing portion 41 together with the rack 46. The plurality of sample containers 13 related to the same subject 10 may be set in one rack 46, but in the following description, it is assumed that the sample containers 13 set in the rack 46 are submitted by different subjects 10.

Figure 5:
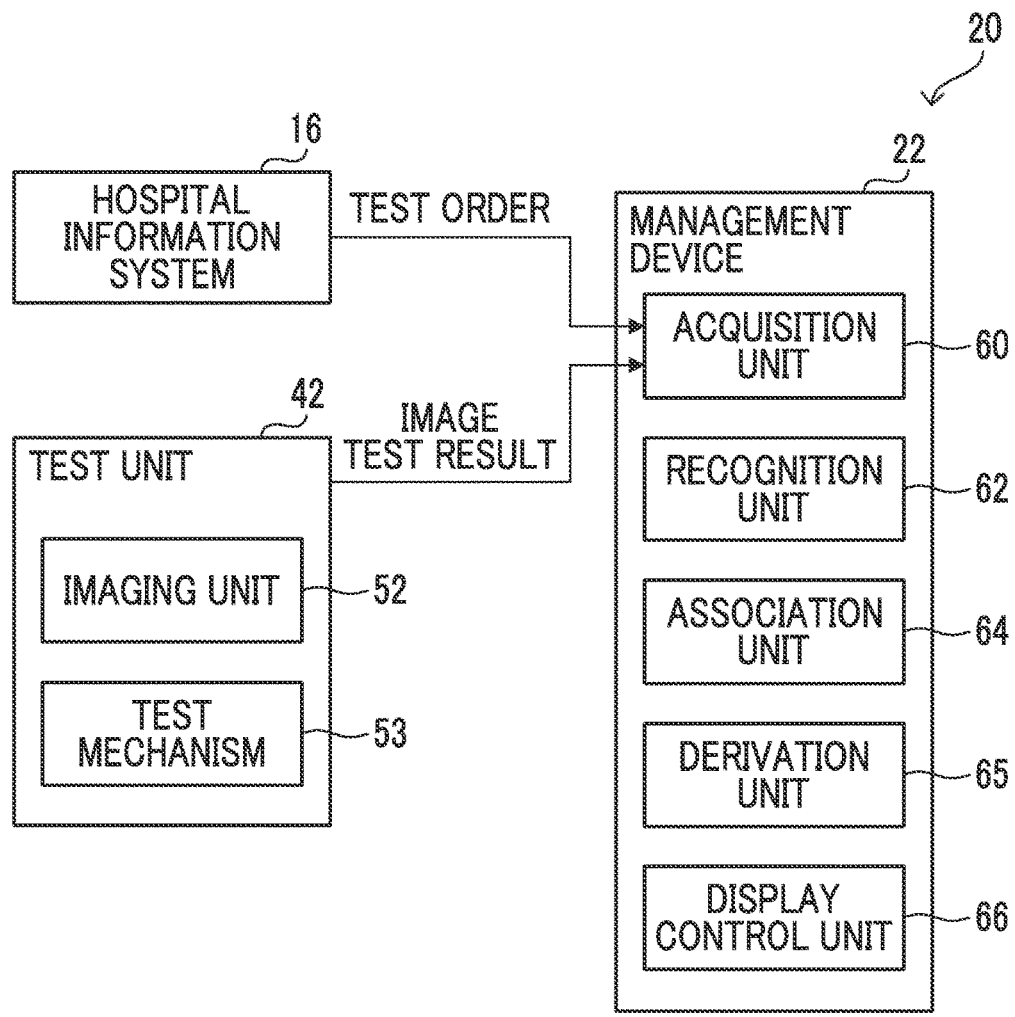
FIG. 5 is a block diagram showing an example of a functional configuration of the management device according to each embodiment.

As shown in FIG. 5, the test unit 42 comprises an imaging unit 52 and a test mechanism 53. The test mechanism 53 is a mechanism for sequentially performing a fecal occult blood test on the samples contained in the plurality of sample containers 13 set in the rack 46, and includes a stock of reagents used for the fecal occult blood test. In a case where the test is completed, the test mechanism 53 may control the touch panel 43 to sequentially display the test result, the progress of the test, and the like.

The imaging unit 52 includes an imaging device such as a camera. The imaging unit 52 images an area including the subject information and the relevant information given to the outer surface of the sample container 13 to obtain an image 55 at the timing of providing the sample contained in each sample container 13 to the test mechanism 53. Specifically, the image 55 is obtained by imaging an area including the label 35 on which the subject information and the collection date information are entered and the temperature detection material 38. The imaging unit 52 may image the plurality of sample containers 13 set in the rack 46 individually, or image some or all of the plurality of sample containers 13 set in the rack 46 together.

The test device 21 outputs a test result obtained by the test mechanism 53 and the image 55 of the sample container 13 in which the sample for which the test result is obtained is contained to the management device 22 in association with each other (see FIG. 8).

An ID (IDentifier) may be given to the rack 46 by using a barcode, an IC chip, or the like (not shown) so that the test device 21 can individually recognize the rack 46. According to such a form, the sample container 13 and the test result can be managed for each rack 46, so that confusion can be suppressed.

Figure 4:
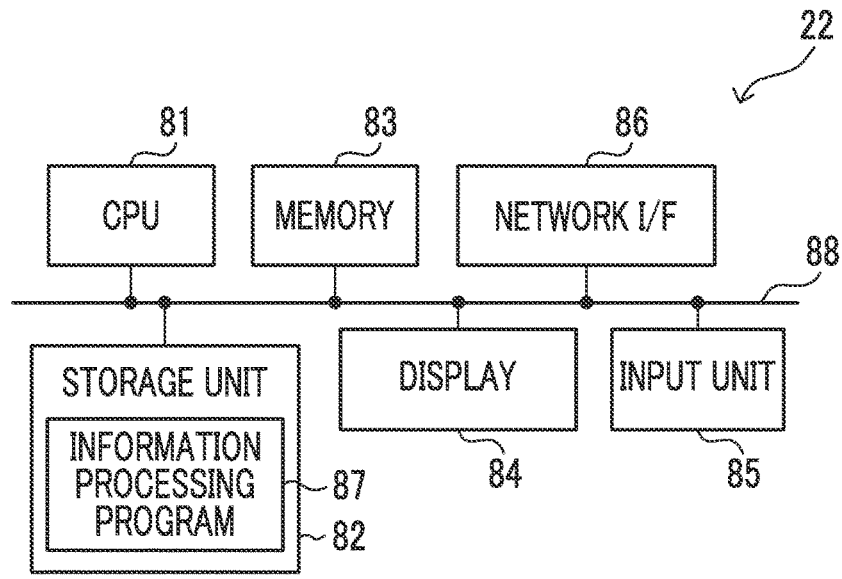
FIG. 4 is a block diagram showing an example of a hardware configuration of a management device according to each embodiment.

Next, a hardware configuration of the management device 22 according to the present embodiment will be described with reference to FIG. 4. As shown in FIG. 4, the management device 22 includes a CPU 81, a non-volatile storage unit 82, and a memory 83 as a temporary storage area. Further, the management device 22 includes a display 84 such as a liquid crystal display and an organic electro luminescence (EL) display, an input unit 85 such as a keyboard and a mouse, and a network interface (I/F) 86 connected to a network. The CPU 81, the storage unit 82, the memory 83, the display 84, the input unit 85, and the network I/F 86 are connected to a bus 88. The CPU 81 is an example of the processor in the present disclosure.

The storage unit 82 is realized by a storage device such as a hard disk drive (HDD), a solid state drive (SSD), and a flash memory. An information processing program 87 is stored in the storage unit 82 as the storage medium. The CPU 81 reads out the information processing program 87 from the storage unit 82, loads the read-out program into the memory 83, and executes the loaded information processing program 87.

Next, a functional configuration of the management device 22 according to the present embodiment will be described with reference to FIGS. 5 to 12. As shown in FIG. 5, the management device 22 includes an acquisition unit 60, a recognition unit 62, an association unit 64, a derivation unit 65, and a display control unit 66. The CPU 81 executes the information processing program 87, and thus, the management device 22 functions as the acquisition unit 60, the recognition unit 62, the association unit 64, the derivation unit 65, and the display control unit 66.

As shown in FIG. 5, the acquisition unit 60 acquires a test order from the hospital information system 16. FIG. 6 shows an example of a test order. As shown in FIG. 6, the test order includes subject information of the subject 10 who performs a test, that is, the subject 10 who collects a sample. In the example of FIG. 6, the subject information includes information such as the name, gender, and age of the subject 10, and a subject ID assigned to each subject 10. In addition to the subject information, the test order may include information indicating the target and contents of the test to be performed.

The test order is created for each group to which the subject belongs, such as a company and a school. FIG. 6 shows an example in which test orders are created for each of "Company P" and "Company Q" as an example of the group. The test order may include information on the group to which the subject belongs as the subject information.

As shown in FIG. 7, the tester sets the plurality of sample containers 13 to be tested in the rack 46 and causes the test device 21 to test the samples. The order in which the sample containers 13 are arranged on the rack 46 is random, and may be different from the order registered in the test order.

The acquisition unit 60 acquires the test result and the image 55 from the test device 21. As described above, the test result and the image 55 are output from the test device 21 in association with each other as shown in FIG. 8. In the example of FIG. 8, a "measured value" is shown as an example of the test result. In addition, the example of FIG. 8 also includes a "test ID" corresponding to the image 55 and the test result. The "test ID" represents the order in which the tests were performed (or the order in which the test results were acquired), and is attached to, for example, a set of the test result and the image 55 in a case where the acquisition unit 60 acquires the test result and the image 55 corresponding to each other.

The recognition unit 62 recognizes the subject information and the relevant information given to each sample container 13 based on the image 55. Specifically, the recognition unit 62 has a character recognition function such as optical character recognition/reader (OCR). FIG. 9 shows the result of the recognition unit 62 recognizing the subject information including the information such as the name, gender, and age included in the image 55, the collection date information as relevant information 106, and the information on the maximum-reached temperature indicated by the temperature detection material 38. In addition, "–" in the field of the maximum-reached temperature in FIG. 9 means the result of the recognition unit 62 recognizing that the maximum-reached temperature is lower than 50 degrees based on the image of the temperature detection material 38 included in the image 55.

The derivation unit 65 derives reliability information 108 indicating the reliability of the test result related to the sample based on the relevant information 106 (for example, the collection date information and the information on the maximum-reached temperature) recognized by the recognition unit 62. The reliability information 108 is, for example, information indicating the degree to which the test result related to the sample can be relied on (hereinafter, referred to as "degree of reliability"), or whether or not the test result related to the sample is reliable.

Specifically, the storage unit 82 of the management device 22 may have a table in which the derivation criteria for deriving the reliability information 108 based on the relevant information 106 recognized by the recognition unit 62 are recorded for each type of the sample. In this case, the derivation unit 65 derives reliability information 108 of a test result related to a corresponding sample based on the derivation criteria recorded in the table.

FIG. 10 is a diagram showing an example of tables T1 and T2 in which derivation criteria for deriving the degree of reliability as an example of reliability information 108 are recorded for each type of the sample. In FIG. 10, the table T1 is a table used for a fecal occult blood test, and the table T2 is a table used for a blood test. As shown in FIG. 10, in the tables T1 and T2, the degree of reliability corresponding to each of the number of elapsed days obtained from the collection date information as an example of the relevant information 106 and information on the maximum-reached temperature as an example of the relevant information 106 is determined. Here, the degree of reliability means that the larger the numerical value, the higher the degree of reliability of the test result related to the sample.

A specific example of deriving the degree of reliability from the table T1 will be described with reference to FIGS. 9 and 10 in a case where the test type is a fecal occult blood test and the test implementation date is Apr. 30, 2019. For a sample with a test ID "0001" in FIG. 9, the derivation unit 65 calculates that the number of elapsed days is 5 days from the collection date information ("Apr. 25, 2019"). Further, the derivation unit 65 refers to the table T1 of the fecal occult blood test of FIG. 10, and derives the degree of reliability "80" in a case where the number of elapsed days is 5 days and the maximum-reached temperature is 50 degrees as the degree of reliability of the test result related to the sample with the test ID "0001". For a sample with a test ID "0002" in FIG. 9, the derivation unit 65 calculates that the number of elapsed days is 8 days from the collection date information ("Apr. 22, 2019"). Further, the derivation unit 65 refers to the table T1 of the fecal occult blood test of FIG. 10, and derives the degree of reliability "60" in a case where the number of elapsed days is 8 days and the maximum-reached temperature is 50 degrees as the degree of reliability of the test result related to the sample with the test ID "0002".

The method of deriving the degree of reliability by the derivation unit 65 is not limited to the method using the table described above. For example, the degree of reliability may be derived by a mathematical formula with a numerical value obtained based on the relevant information 106, such as the number of elapsed days obtained from the collection date information and the information on the maximum-reached temperature, as variables. Further, the derivation unit 65 may derive the result of determining whether or not each test result is reliable as the reliability information 108 by comparing the numerical value obtained based on the relevant information 106 with a predetermined threshold value for each relevant information 106.

As shown in FIG. 11, the association unit 64 associates the test result related to the sample contained in each sample container 13 with a test order including the subject information, based on the subject information recognized by the recognition unit 62 (see FIG. 9) and the test order (see FIG. 6).

Here, the "association" between the test result and the test order refers to specifying the test result related to the sample of the specific sample container 13 as the test result related to the specific test order. In other words, the "association" is substantially synonymous with specifying the specific sample container 13 as the sample container 13 related to the specific test order, and identifying that the specific subject 10 who provided the sample of a specific sample container 13 is the subject 10 related to the specific test order. This is because, in a case where one of these is associated, the other is automatically determined. Further, since the sample container 13 has a one-to-one correspondence with the image 55, the association between the sample container 13 and the test order can be rephrased as the association between the image 55 and the test order.

Specifically, the association unit 64 collates a part or all of the recognition result of the recognition unit 62 with the corresponding item of the test order. Then, as shown in FIG. 11, the test order in which contents of the subject information included in the recognition result and the test order in common match each other is associated with the image 55, the test result, and the reliability information 108.

In addition, in a case where there is no test order in which the contents of the subject information included in the recognition result and the test order in common match each other, the association unit 64 may associate a test order having a high match rate among the partially matching test orders with the set of the image 55, the reliability information 108, and the test result. That is, the association unit 64 may collate the recognition result of the image 55 with the test order, and presume that the test order having a good match rate (for example, the highest match rate) of the subject information is the test order corresponding to the set of the image 55, the test result, and the reliability information 108 to perform association. In this case, even in a case where the image 55 is poorly recognized, the association that is tentatively considered to be the most accurate can be performed.

Further, in a case where the recognition unit 62 recognizes plural pieces of subject information, the association unit 64 may set a priority among the pieces of subject information. For example, in a case where the recognition unit 62 recognizes the name, gender, and age of the subject 10 from the image 55, the association unit 64 may prioritize the name of the subject 10 among these information and associate the name with the test order. Since the probability that the name of the subject 10 matches the other subject 10 is lower than the probability that the gender and age match the other subject 10, by giving priority to the match rate of names, it becomes easy to make an accurate association even in a case where the subject information does not completely match.

As shown in FIG. 12, the display control unit 66 performs control such that the test result and its reliability information 108 (for example, the degree of reliability), the test order, the image 55 are displayed on the display 84 in association with each other. The display of some of the reliability information 108, the test order, and the image 55 may be omitted. Further, the management device 22 may transmit a test result report as shown in FIG. 12 to the hospital information system 16 or the like of the hospital 11.

In addition, as shown in FIG. 12, the display control unit 66 may perform control such that the test result and a comment 110 added based on the reliability information 108 (for example, the degree of reliability) related to the test result are displayed on the display 84 in association with each other. For example, comments according to the degree of reliability may be stored in the storage unit 82 in advance, and the display control unit 66 may control the display by adding a comment 110 according to the degree of reliability together with the test result. FIG. 12 shows an example in which a sentence indicating whether the test result is accurate or is likely to be inaccurate is added as the comment 110 according to the degree of reliability.

Figure 13:
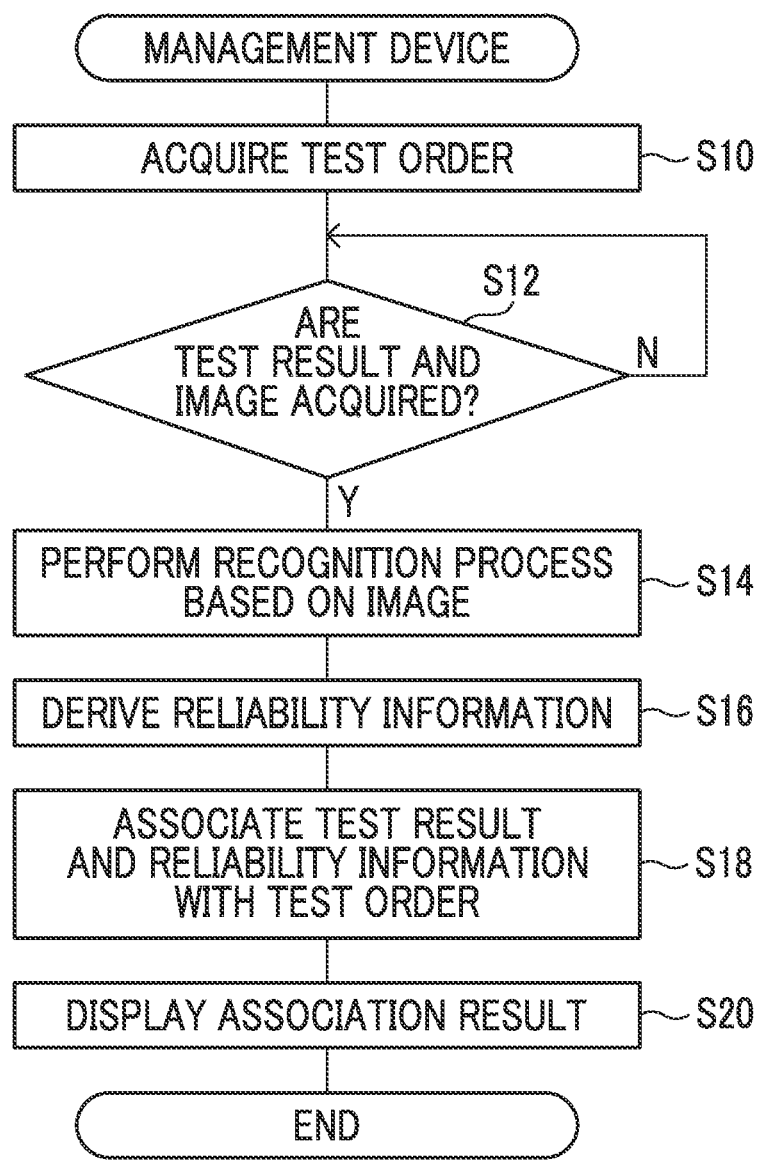
FIG. 13 is a flowchart showing an example of a process in the management device.

Next, an operation of the management device 22 according to the present embodiment will be described with reference to FIG. 13. The CPU 81 executes the information processing program 87, and thus, the process shown in FIG. 13 is executed. The process shown in FIG. 13 is executed in a case where, for example, an operator such as a tester inputs an instruction to start a test via the input unit 85.

In Step S10 of FIG. 13, the acquisition unit 60 acquires a test order from the hospital information system 16. In Step S12, the acquisition unit 60 waits until the test result and the image 55 are acquired from the test device 21.

Here, the process performed by the test device 21 between the above-mentioned Steps S12 and S14 will be described with reference to FIG. 14. The process shown in FIG. 14 is executed in a case where, for example, an operator such as a tester inputs an instruction to start a test via the touch panel 43.

Figure 14:
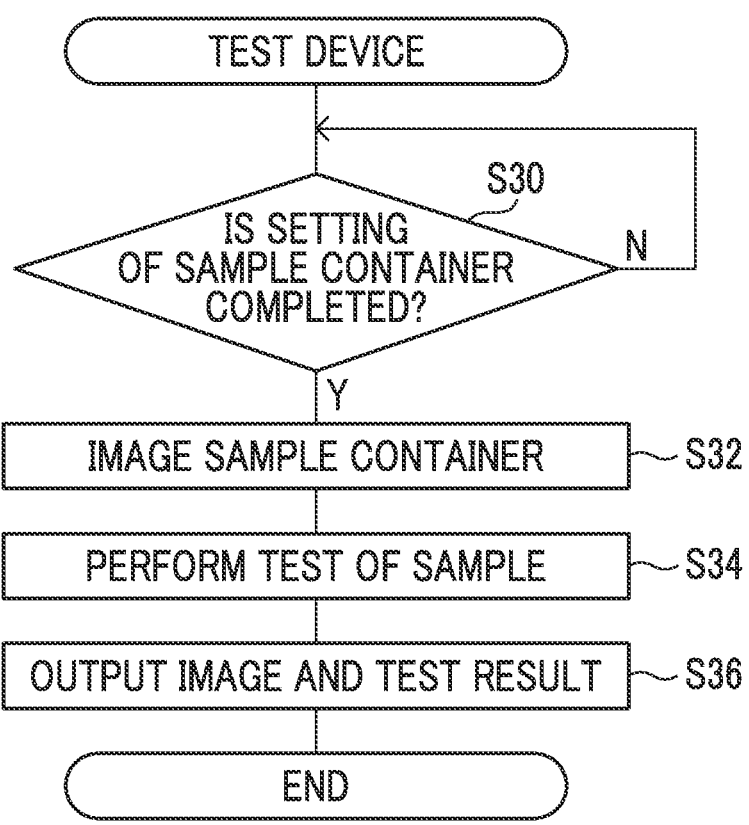
FIG. 14 is a flowchart showing an example of a process in the test device.

In Step S30 of FIG. 14, the test device 21 determines whether or not the sample container 13 is set in the sample container placing portion 41. In a case where the sample container 13 is set in the sample container placing portion 41 (Step S30 is Y), in Step S32, the imaging unit 52 images the sample container 13 to obtain the image 55 including the subject information and the relevant information 106. In Step S34, the test mechanism 53 performs the test of the sample. In Step S36, the test device 21 outputs the image 55 obtained in Step S32 and the test result obtained in Step S34 in association with each other to the management device 22. The process of Step S32 and the process of Step S34 may be performed in parallel or may be performed in a different order.

Referring back to FIG. 13, a description will be given. In Step S14 of FIG. 13, the recognition unit 62 recognizes the subject information and the relevant information 106 given to each sample container 13 based on the image 55 acquired in Step S12. In Step S16, the derivation unit 65 derives the reliability information 108 of the test result acquired in Step S12 based on the relevant information 106 recognized in Step S14.

In Step S18, the association unit 64 associates the test result acquired in Step S12 and the reliability information 108 derived in Step S16 with the test order based on the subject information recognized in Step S14 and the test order acquired in Step S10. In Step S20, the display control unit 66 performs control such that the test result and the reliability information 108 and the test order associated in Step S18 are displayed on the display 84 in association with each other.

As described above, the management system 20 according to the present embodiment is a management system including at least one processor, and the processor is configured to acquire the image 55 obtained by imaging the sample container 13 containing the sample. Further, the processor is configured to recognize the relevant information 106 related to the reliability of the test result related to the sample based on the image 55, and derive reliability information 108 indicating the reliability of the test result related to the sample based on the recognized relevant information 106. With the management system 20 according to the present embodiment, based on the image 55 obtained by imaging the sample container 13, the relevant information 106, that is, information regarding a factor that may reduce the reliability of the test result related to the sample can be recognized. Therefore, information indicating the reliability of the test result can be derived.

In the above embodiment, a form in which the technique for deriving the information indicating the reliability of the test result is applied to the management system 20 in which the management device 22 recognizes the subject information and associates the test result with the test order has been described, but the present disclosure is not limited thereto. For example, a technique for deriving information indicating the reliability of the test result of the present disclosure may be applied to the management system in which the barcode issued based on the test order is manually attached to the corresponding sample container and the test result is associated with the test order by a unit such as reading the barcode at the time of testing the sample.

Further, in the above embodiment, a form in which the sample container 13 submitted by the subject 10 is sent to the testing institution 12 via the hospital 11 has been described, but the present disclosure is not limited thereto. In recent years, the number of personal tests in which the subject 10 himself/herself collects a sample and mails the sample directly to the testing institution 12 is increasing, and the technique of the present disclosure is also applicable to such a personal test.

Further, in the above embodiment, a form in which the temperature detection material 38 is given to all of the sample containers 13 to which the test is to be performed has been described, but the present disclosure is not limited thereto. As described above, in a case where the sample container 13 submitted by the subject 10 is sent to the testing institution 12 via the hospital 11, usually, the sample container 13 is sent collectively for each group to which the subject 10 belongs, for example, a company or a school. That is, the temperature conditions during the time at which the sample container 13 is sent from the hospital 11 to the testing institution 12 are the same within the group.

Therefore, in a case where the plurality of the sample containers 13 are divided into groups, the temperature detection material 38 may be given to at least one sample container 13 included in the group. In a case where the temperature detection material 38 is given to at least one sample container 13 included in the group, for all the sample containers 13 included in the group, it is possible to grasp the maximum-reached temperature in the environment placed while being sent from the hospital 11 to the testing institution 12. In this case, the derivation unit 65 derives the reliability information 108 by using the recognized information on the maximum-reached temperature for the sample container 13 to which the temperature detection material 38 is given as information on a maximum-reached temperature for the other sample container 13 included in the group including the sample container 13. According to such a form, the consumption of the temperature detection material 38 can be suppressed, which is advantageous in reducing the cost.

Further, in the above embodiment, at least one information of the amount or color of the sample may be used as the relevant information 106 recognized by the recognition unit 62, and the derivation unit 65 may derive the reliability information 108 based on the recognized at least one information of the amount or color of the sample. In a case where the amount of sample is insufficient, the test cannot be performed appropriately and the reliability of the test result may be lowered. Further, in the fecal occult blood test, the storage solution and/or the diluent evaporates and leaks, so that the test cannot be performed appropriately and the reliability of the test result may be lowered. Further, in the fecal occult blood test, as the amount of the sample is insufficient, the change from the original color of the storage solution and/or the diluent becomes smaller, so that the reliability of the test result can also be determined by the color of the storage solution and/or the diluent.

Figure 15:
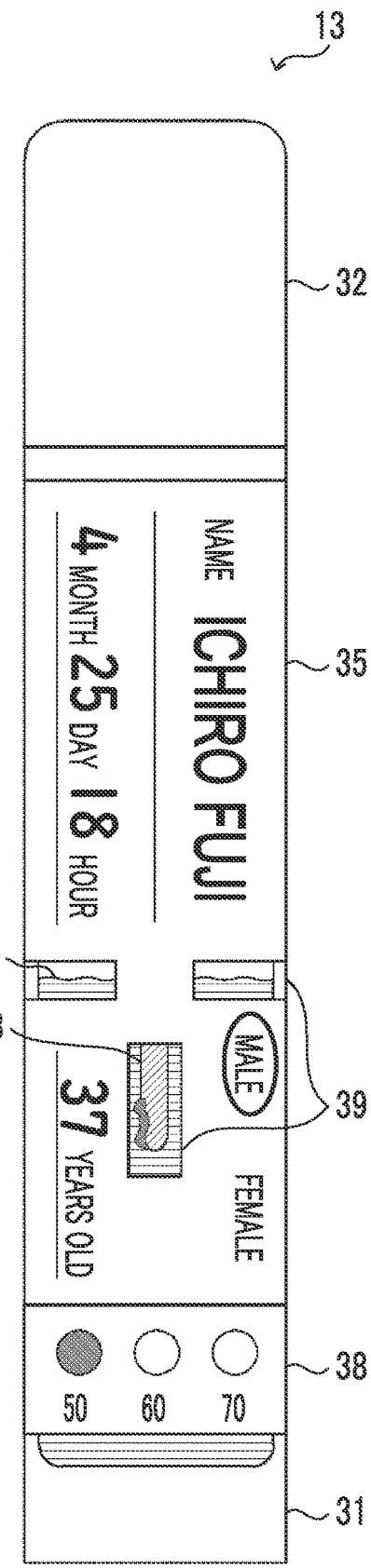
FIG. 15 is a diagram showing an example of a sample container for a fecal occult blood test.

Further, as the sample container 13 for recognizing the amount and the color of the sample, for example, the sample container including a transparent portion 39 which is at least a part of the sample container 13 and is formed to be transparent or translucent so that at least one of the amount or the color of the sample contained in the sample container 13 can be checked may be used. For example, as described above, the sample container 13 in which the entire container body 31 is transparent or translucent is included in this. Further, for example, the entire container body 31 is opaque, and the transparent portion 39 formed to be transparent or translucent may be provided only at a partial position where at least one of the amount or the color of the sample can be checked. Further, for example, as shown in FIG. 15, the transparent portion 39 of the sample container 13 may be checked by an insertion part 33 for collecting feces and a label 35 provided with an opening portion and/or a notch portion at a position where a liquid level 34 of the storage solution of feces and/or the diluent can be checked.

In these cases, the image 55 captured by the imaging unit 52 of the test device 21 includes the transparent portion 39 as well as the label 35 and the temperature detection material 38. Therefore, the recognition unit 62 can recognize, from the transparent portion 39 included in the image 55, the color and amount of the sample attached to the insertion part 33, and the color and the height of the liquid level 34 of the storage solution of feces and/or the diluent (that is, the amount of the storage solution and/or the diluent).

Further, for example, a surface of the sample container 13 to which the label 35 is not attached is formed transparent or translucent, and the surface is separately imaged to obtain an image, so that the recognition unit 62 may be able to recognize at least one of the amount or the color of the sample contained in the sample container 13 based on the image.

Further, in the above embodiment, by imaging the area including the cap 32 of the sample container 13 to obtain the image 55, as the relevant information 106 recognized by the recognition unit 62, information on whether or not the cap 32 of the sample container 13 is appropriately closed may be used. In a case where the cap 32 is not appropriately closed, the sample leaks from the sample container 13 and the amount of the sample is reduced, so that the test cannot be performed appropriately and the reliability of the test result may be lowered.

Further, in the above embodiment, the management device 22 or the test device 21 may determine whether or not to perform the test related to the sample contained in the sample container 13 based on the reliability information 108. Specifically, for example, in the test device 21, after the imaging unit 52 obtains the image 55, the test unit 42 may recognize the relevant information 106 based on the image 55 and derive the reliability information 108 to determine whether or not to perform the test. That is, in the above embodiment, the process performed by the recognition unit 62 and the derivation unit 65 of the management device 22 may be performed by the test device 21 before the sample is tested. For example, the test device 21 may determine that the test is not performed in a case where the degree of reliability of the derived reliability information 108 is lower than a predetermined threshold value. In this case, the test device 21 does not have to perform a test on the sample container 13 determined not to be tested.

Further, for example, before setting the sample container 13 in the test device 21, an external imaging device images the sample container 13 to obtain the image 55, and then the management device 22 may recognize the relevant information 106 based on the image 55 and derive the reliability information 108. That is, the derivation unit 65 may derive the reliability information 108 before testing the sample in the test device 21, determine whether or not to perform a test related to the sample contained in the sample container 13, and notify the test device 21 of a determination result thereof. In this case, the test device 21 does not have to perform a test on the sample container 13 that has been notified that the test is not performed. Further, the display control unit 66 may display the sample container 13 determined not to be tested on the display 84 so as to be discriminateable. In this case, a tester may visually check the display 84 and prevent the sample container 13 determined not to be tested from being set in the test device 21.

Further, in the above embodiment, in a case where the recognition unit 62 cannot recognize the subject information and/or relevant information based on the image 55, or recognizes that the image 55 does not include the subject information and/or relevant information, reliability information indicating that fact may be derived. For example, the degree of reliability may be derived as 0, or the determination result that the degree of reliability may be unreliable may be derived. Further, in these cases, the recognition unit 62 may perform control to issue a warning to the tester. Control to issue a warning includes, for example, displaying a warning on the display 84 and emitting a sound in a case where the management device 22 comprises a speaker.

Second Embodiment

In the present embodiment, in order to more appropriately associate the test result with the test order, an example of a form in which information regarding the group to which the subject 10 belongs is further used in addition to the discrimination image 72 will be described. Hereinafter, the same components as those in the first embodiment will be designated by the same symbols, and the description thereof will be omitted.

Usually, the test in the test device 21 is performed in the order of test order by the tester setting the sample container 13 in the rack 46 for each test order (that is, for each group). On the other hand, in order to improve the efficiency of the test work, especially in a case where the rack 46 has an empty space, it is desired that the sample containers 13 included in plural different groups are set in the same rack 46 and continuously tested. In such a case, in a case where the boundary between the groups can be determined, it is possible to specify a group to which each sample container 13 belongs.

Therefore, in the present embodiment, in a case where the plurality of sample containers 13 are divided into groups and samples are continuously tested for plural groups, the boundary between the groups is determined by using a boundary container in which the group boundary information 102 indicating the boundary between the plurality of groups is given on the outer surface. The group boundary information 102 may include group discrimination information 104 for discriminating the group to which the subject 10 belongs. The group boundary information 102 and the group discrimination information 104 are represented by at least one of a character or a symbol.

The boundary container is, for example, a sample container 13 containing a sample to be tested at at least one of first or last in the group. Hereinafter, an example in which the group boundary information 102 is given to the outer surface of the sample container 13 containing the sample to be tested first in each group as an example of the boundary container will be described.

Figure 16:
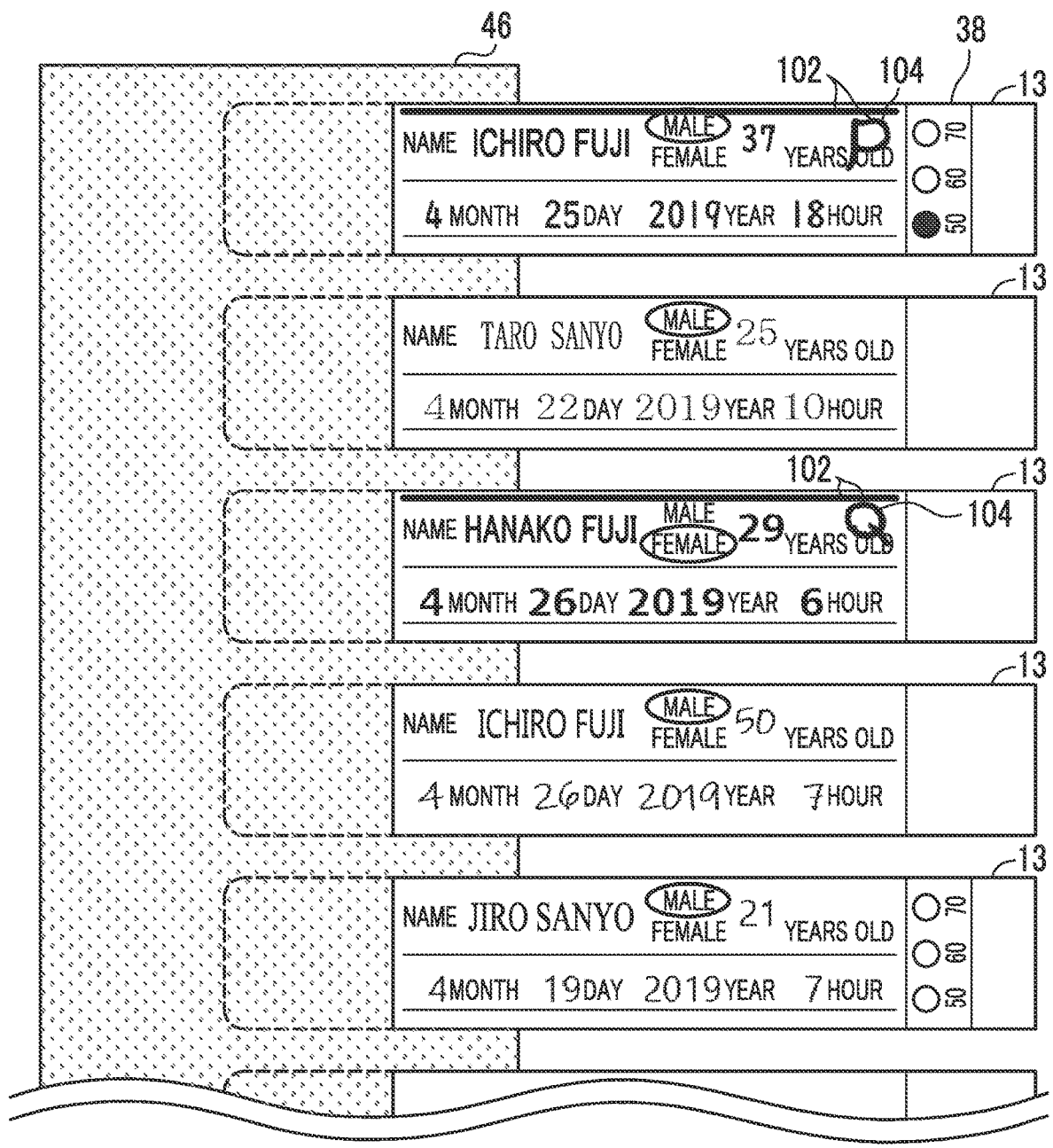
FIG. 16 is a diagram showing an example of a sample container to which group boundary information is given.

FIG. 16 shows an example in which one line as an example of the group boundary information 102 and the characters "P" and "Q" are given to the first sample container 13 of each group of company P and company Q, respectively. Of these, the characters "P" and "Q" also function as the group discrimination information 104 for discriminating the groups of company P and company Q, respectively.

As shown in FIG. 16, the tester gives the group boundary information 102 to the first sample container 13 of the group, sets the information in the rack 46, and executes the test by the test device 21. The sample container 13 is set in the rack 46 in the order of test order so that company P comes first and company Q comes later, for example, as a bundle for each group. That is, the test is performed for each group in the order of test order. The order in which the sample containers 13 are arranged in each group is random, and may be different from the order registered in the test order.

The acquisition unit 60 acquires the test result and the image 55 from the test device 21. The image 55 includes the subject information, the relevant information 106, and the group boundary information 102. Further, the group boundary information 102 may include the group discrimination information 104.

The recognition unit 62 recognizes the subject information and the relevant information 106 given to each sample container 13 and the group boundary information 102 given to the boundary container based on the image 55. Further, in a case where the group boundary information 102 includes the group discrimination information 104, the recognition unit 62 recognizes the group discrimination information 104.

As shown in FIG. 17, the association unit 64 determines that the sample container 13 recognized that the group boundary information 102 is given to the image 55 is the first sample container 13 of each group of company P and company Q. The association unit 64 associates a test result related to the sample contained in each of the sample containers 13 with the test order in which the group is divided corresponding to the group boundary information 102, based on the recognition result of the recognition unit 62 and the test order.

Here, the "test order in which the group is divided corresponding to the group boundary information 102" means, for example, the test order created for each group as described above. Further, for example, it means a test order in which information on the group to which the subject 10 belongs is included for each of the plurality of subjects 10. Further, for example, in a case where one test order includes plural groups, it means the test order including the information indicating the boundary of the group represented by a predetermined character string and blanks at the boundary between the groups.

As described above, the test is performed for each group in order of test order. Therefore, even in a case where the group boundary information 102 does not include the group discrimination information 104, the group boundary information 102 shows the boundary between the groups, so that a group to which each sample container 13 belongs can be specified.

Further, in a case where the group boundary information 102 includes the group discrimination information 104, the association unit 64 associates a test result related to the sample contained in each of the sample containers 13 with the test order further including the group discrimination information 104, based on the recognition result of the recognition unit 62 and the test order. In this case, by collating the group discrimination information 104 recognized from the image 55 with the group discrimination information 104 (for example, "Company P" and "Company Q") included in the test order, each of the plurality of subjects 10 can be associated with each other.

In a case where the plurality of the sample containers 13 are divided into groups as in the present embodiment, the temperature detection material 38 may be given to at least one sample container 13 included in the group. As described above, in a case where the sample container 13 submitted by the subject 10 is sent to the testing institution 12 via the hospital 11, usually, the sample container 13 is sent collectively for each group to which the subject 10 belongs, for example, a company or a school. That is, the temperature conditions during the time at which the sample container 13 is sent from the hospital 11 to the testing institution 12 are the same within the group. Therefore, in a case where the temperature detection material 38 is given to at least one sample container 13 included in the group, for all the sample containers 13 included in the group, it is possible to grasp the maximum-reached temperature in the environment placed while being sent from the hospital 11 to the testing institution 12.

In this case, the derivation unit 65 derives reliability information of the test result related to each sample by using the recognized information on the maximum-reached temperature for the sample container 13 to which the temperature detection material 38 is given as information on a maximum-reached temperature for the other sample container 13 included in the group including the sample container 13. According to such a form, the consumption of the temperature detection material 38 can be suppressed, which is advantageous in reducing the cost.

In the example of FIG. 16, the temperature detection material 38 is given to the sample container 13 of "Ichiro Fuji" at company P and the sample container 13 of "Jiro Sanyo" at company Q, respectively. In FIG. 17, the maximum-reached temperature of each sample contained in company P is unified to "50" degrees, which is a maximum-reached temperature of "Ichiro Fuji" of company P, and the maximum-reached temperature of each sample contained in company Q is unified to "–", which is a maximum-reached temperature of "Jiro Sanyo" of company Q.

As described above, in the management system 20 according to the present embodiment, in a case where the plurality of sample containers 13 are divided into groups and the samples are continuously tested for the plurality of groups, group boundary information 102 indicating a boundary between the plurality of groups is further given to the outer surface of the sample container 13 containing a sample to be tested at at least one of first or last in the group. Further, the processor is configured to recognize the group boundary information 102 based on the image, and associate a test result related to the sample contained in each of the sample containers 13 with the test order in which the group is divided corresponding to the group boundary information 102, based on a result of the recognition and the test order.

With the management system 20 according to the present embodiment, it is possible to determine the boundary between groups without giving an identification unit such as a barcode to the sample container 13 as in the related art. Therefore, it is possible to more appropriately associate the test result with the test order. Further, even though plural sample containers 13 included in each of plural different test orders are collectively set in the test device, the test result and the test order can be appropriately associated with each other.

As the boundary container, for example, a dummy container 14 which does not contain a sample can be used in addition to the sample container 13 to which the group boundary information 102 is given as described above. FIG. 18 is a diagram showing an example in which a dummy container 14 in which no subject information is entered is used as an example. The dummy container 14 may have a shape that can be stored in the test device 21 for testing the sample contained in the sample container 13, and preferably has the same shape as the sample container 13.

In this case, the fact that the subject information is not entered on the outer surface of the dummy container 14 may be used as the group boundary information 102. The association unit 64 determines the boundary of the group by the sample container 13 recognized that the subject information is not given to the image 55.

Figures 19, 20, 21:
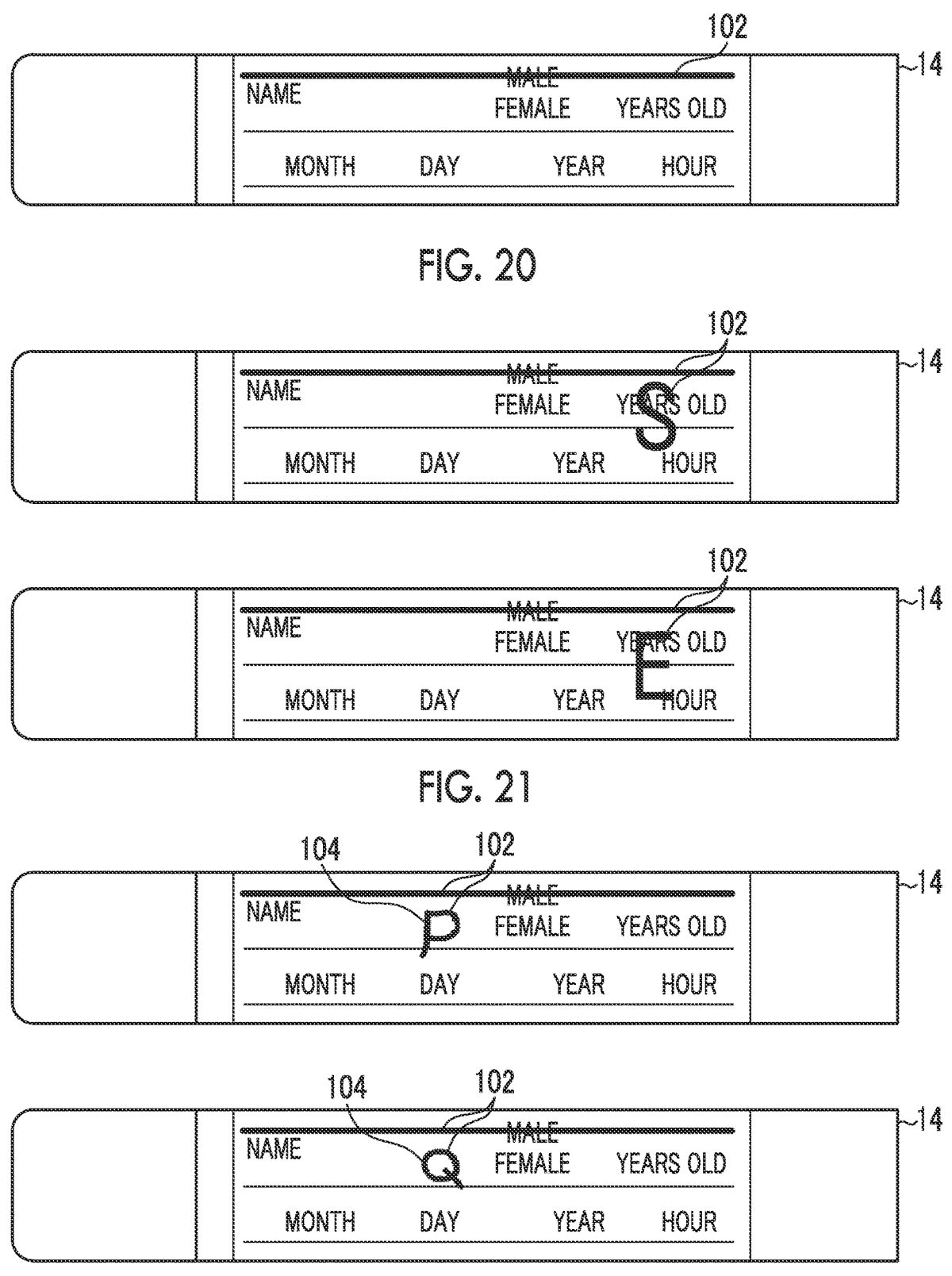

As shown in FIGS. 19 to 21, the group boundary information 102 and the group discrimination information 104 represented by at least one of a character or a symbol may be given to the dummy container 14. FIG. 19 shows an example of the dummy container 14 to which one line is given as an example of the group boundary information 102. FIG. 20 shows the dummy container 14 to which one line as an example of the group boundary information 102 and the characters "S" meaning the beginning of the group and "E" meaning the end of the group are given. FIG. 21 shows the dummy container 14 to which one line as an example of the group boundary information 102, and the characters "P" and "Q" are given. Of these, the characters "P" and "Q" also function as the group discrimination information 104 for discriminating the groups of company P and company Q, respectively.

As described above, according to the form in which the dummy container is used, by giving the group boundary information 102 to the sample container 13, it is possible to suppress the difficulty in recognizing the subject information and the relevant information 106. Therefore, it is possible to more appropriately derive the reliability information and associate the test result with the test order. Further, by preparing the dummy container 14 in advance, the work of giving the group boundary information 102 to the sample container 13 by the tester can be omitted, so that the efficiency of the test work can be improved.

In each of the above embodiments, each functional unit included in the test device 21 and the management device 22 may be performed by an external device connected to the test device 21 and the management device 22. For example, the test device 21 may not include the imaging unit 52, the test device 21 may receive the image 55 captured by an external imaging device such as a digital camera, and the received image 55 may be output in association with the test result. Further, for example, the management device 22 may not include the recognition unit 62, and the management device 22 may receive the subject information, the relevant information 106, the group boundary information 102, and the group discrimination information 104 obtained by causing an external device having a character recognition function to recognize the image 55.

In each of the above embodiments, for example, as hardware structures of processing units that execute various kinds of processing, such as the acquisition unit 60, the recognition unit 62, the association unit 64, the derivation unit 65, and the display control unit 66, various processors shown below can be used. As described above, the various processors include a programmable logic device (PLD) as a processor of which the circuit configuration can be changed after manufacture, such as a field programmable gate array (FPGA), a dedicated electrical circuit as a processor having a dedicated circuit configuration for executing specific processing such as an application specific integrated circuit (ASIC), and the like, in addition to the CPU as a general-purpose processor that functions as various processing units by executing software (program).

One processing unit may be configured by one of the various processors, or configured by a combination of the same or different kinds of two or more processors (for example, a combination of plural FPGAs or a combination of the CPU and the FPGA). In addition, plural processing units may be configured by one processor. As an example where plural processing units are configured by one processor, first, there is a form in which one processor is configured by a combination of one or more CPUs and software as typified by a computer, such as a client or a server, and this processor functions as plural processing units. Second, there is a form in which a processor for realizing the function of the entire system including plural processing units by one integrated circuit (IC) chip as typified by a system on chip (SoC) or the like is used. As described above, various processing units are configured by using one or more of the above-described various processors as hardware structures.

Furthermore, as the hardware structure of the various processors, more specifically, an electrical circuit (circuitry) in which circuit elements such as semiconductor elements are combined can be used.

The following additional remarks will be further disclosed with respect to each of the above embodiments.

Additional Remark 1

A management system comprising at least one processor, in which the processor is configured to
acquire an image obtained by imaging a sample container which contains a sample and in which subject information of a subject from whom the sample is collected is given to an outer surface,
recognize whether or not the subject information is appropriately given based on the image, and determine whether or to perform a test related to the sample based on the recognized result.

Additional Remark 2

A sample container containing a sample and comprising a transparent portion formed to be transparent or translucent so that at least one of an amount or a color of the sample can be checked.

Additional Remark 3

The sample container according to Additional remark 2, in which
the sample includes a liquid sample, and
the transparent portion is arranged at a height position of a predetermined liquid level of the sample.

Additional Remark 4

The sample container according to Additional remark 2 or 3, further comprising:
a collection portion which collects the sample by bringing into contact with the sample,
in which the transparent portion is arranged at a position where the sample attached to the collection portion can be checked.

Additional Remark 5

A label attached to a sample container containing a sample and comprising a transparent portion formed to be transparent or translucent so that at least one of an amount or a color of the sample can be checked,
in which at least one of an opening portion or a notch portion is formed at a position corresponding to the transparent portion.

Additional Remark 6

The label according to Additional remark 5, in which
the sample includes a liquid sample, and
at least one of the opening portion or the notch portion is formed at a height position of a predetermined liquid level of the sample.

Additional Remark 7

The label according to Additional remark 5 or 6, in which
the sample container further comprises a collection portion which collects the sample by bringing into contact with the sample, and
at least one of the opening portion or the notch portion is formed at a position where the sample attached to the collection portion can be checked.

What is claimed is:

1. A management system comprising at least one processor, wherein the processor is configured to
acquire an image obtained by imaging a sample container containing a sample,
recognize relevant information related to reliability of a test result related to the sample based on the image, and
derive reliability information indicating the reliability of the test result related to the sample based on the recognized relevant information,
wherein a temperature detection material which irreversibly indicates a maximum-reached temperature in an environment in which the sample container is placed is given to the sample container, and
the processor is configured to
recognize information on the maximum-reached temperature included in the image as the relevant information, and
derive the reliability information based on the recognized information on the maximum-reached temperature, and
wherein in a case where a plurality of the sample containers are divided into groups, the temperature detection material is given to at least one sample container included in the group, and
the processor is configured to
derive the reliability information by using the recognized information on the maximum-reached temperature for the sample container to which the temperature detection material is given as information on a maximum-reached temperature for the other sample container included in the group including the sample container.

2. The management system according to claim 1, wherein collection date information indicating a collection date on which the sample contained in the sample container is collected is given to an outer surface of the sample container, and
the processor is configured to
recognize the collection date information included in the image as the relevant information, and
derive the reliability information based on the recognized collection date information.

3. The management system according to claim 1, wherein the sample container includes a transparent portion which is at least a part of the sample container and is formed to be transparent or translucent so that at least one of an amount or a color of the sample contained in the sample container is checked, and
the processor is configured to
recognize at least one information of the amount or the color of the sample checked in the transparent portion included in the image as the relevant information, and
derive the reliability information based on the recognized at least one information of the amount or the color of the sample.

4. The management system according to claim 1, further comprising a table in which derivation criteria for deriving the reliability information based on the relevant information are recorded for each type of the sample,
wherein the processor is configured to
derive reliability information of a test result related to a corresponding sample based on the derivation criteria recorded in the table.

5. The management system according to claim 1, wherein the processor is configured to
perform control such that the test result and the reliability information are displayed on a display in association with each other.

6. The management system according to claim 1, wherein the processor is configured to
perform control such that the test result and a comment added based on the reliability information related to the test result are displayed on a display in association with each other.

7. The management system according to claim 1, wherein the processor is configured to
determine whether or not to perform a test related to the sample contained in the sample container based on the reliability information.

8. The management system according to claim 1, wherein subject information of a subject from whom the sample contained in the sample container is collected is given to an outer surface of the sample container, and
the processor is configured to
acquire an image obtained by imaging an area including the subject information given to the sample container,
recognize the subject information given to the sample container based on the image, and
associate a test result related to the sample contained in each of the sample containers with a test order including the subject information, based on the recognized subject information and the test order.

9. The management system according to claim 8, wherein the processor is configured to
- acquire an image obtained by imaging an outer surface of a boundary container in which group boundary information indicating a boundary between a plurality of groups is given to the outer surface in a case where a plurality of the sample containers are divided into groups and samples are continuously tested for the plurality of groups,
- recognize the group boundary information given to the boundary container based on the image, and
- associate the test result related to the sample contained in each of the sample containers with a test order in which the group is divided corresponding to the group boundary information, based on the recognized group boundary information and the test order.

10. The management system according to claim 9, wherein the boundary container is a sample container containing a sample to be tested at at least one of first or last in the group.

11. The management system according to claim 9, wherein the boundary container is a dummy container which does not contain a sample.

12. The management system according to claim 11, wherein a fact that subject information is not entered on an outer surface of the dummy container is used as the group boundary information.

13. The management system according to claim 9, wherein the group boundary information includes group discrimination information for discriminating a group to which the sample container belongs, and
the processor is configured to
- further recognize the group discrimination information based on the image, and
- associate the test result related to the sample contained in each of the sample containers with the test order further including the group discrimination information, based on the recognized group discrimination information and the test order.

14. The management system according to claim 9, wherein the group boundary information is represented by at least one of a character or a symbol.

15. The management system according to claim 8, wherein the processor is configured to
- perform control such that the test result and the test order are displayed on a display in association with each other.

16. A management method comprising:
- acquiring an image obtained by imaging a sample container containing a sample;
- recognizing relevant information related to reliability of a test result related to the sample based on the image;
- deriving reliability information indicating the reliability of the test result related to the sample based on the recognized relevant information,
- wherein a temperature detection material which irreversibly indicates a maximum-reached temperature in an environment in which the sample container is placed is given to the sample container,
- recognizing information on the maximum-reached temperature included in the image as the relevant information,
- deriving the reliability information based on the recognized information on the maximum-reached temperature,
- wherein in a case where a plurality of the sample containers are divided into groups, the temperature detection material is given to at least one sample container included in the group, and
- deriving the reliability information by using the recognized information on the maximum-reached temperature for the sample container to which the temperature detection material is given as information on a maximum-reached temperature for the other sample container included in the group including the sample container.

* * * * *